(12) United States Patent
Vito et al.

(10) Patent No.: US 6,899,669 B2
(45) Date of Patent: May 31, 2005

(54) AUTOLOGOUS VASCULAR GRAFTS CREATED BY VESSEL DISTENSION

(75) Inventors: Raymond P. Vito, NW. Atlanta, GA (US); Jack C. Griffis, III, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 66 days.

(21) Appl. No.: 10/601,963

(22) Filed: Jun. 23, 2003

(65) Prior Publication Data

US 2004/0054354 A1 Mar. 18, 2004

Related U.S. Application Data

(63) Continuation of application No. 09/994,241, filed on Nov. 27, 2001, now Pat. No. 6,663,617, which is a continuation-in-part of application No. 09/322,095, filed on May 28, 1999, now Pat. No. 6,322,553.
(60) Provisional application No. 60/274,909, filed on Mar. 9, 2001, and provisional application No. 60/087,027, filed on May 28, 1998.

(51) Int. Cl.$^7$ .................................................. A61F 2/04
(52) U.S. Cl. ......................................................... 600/36
(58) Field of Search ................................ 600/36; 606/1, 606/159, 194; 623/1.1, 903

(56) References Cited

U.S. PATENT DOCUMENTS

| | | | |
|---|---|---|---|
| 4,836,110 A | 6/1989 | Burczynski | |
| 4,846,181 A | 7/1989 | Miller | |
| 4,863,469 A | 9/1989 | VanBeek et al. | |
| 4,978,348 A | 12/1990 | Ilizarov | |
| 4,990,131 A | 2/1991 | Dardik et al. | |
| 5,078,726 A | 1/1992 | Kreamer | |
| 5,083,576 A | 1/1992 | Ruiz-Razura et al. | |
| 5,122,110 A | * 6/1992 | McNally et al. ............... 600/36 |
| 5,344,425 A | 9/1994 | Sawyer | |
| 5,376,110 A | * 12/1994 | Tu et al. ........................ 600/36 |
| 5,441,540 A | 8/1995 | Kim | |
| 5,549,664 A | 8/1996 | Hirata et al. | |
| 5,556,428 A | 9/1996 | Shah | |
| 5,662,710 A | 9/1997 | Bonutti | |
| 5,702,419 A | 12/1997 | Berry et al. | |
| 5,713,917 A | 2/1998 | Leonhardt et al. | |
| 5,769,893 A | 6/1998 | Shah | |
| 5,879,713 A | 3/1999 | Roth et al. | |
| 5,888,720 A | 3/1999 | Mitrani | |
| 5,899,936 A | 5/1999 | Goldstein | |
| 5,902,228 A | 5/1999 | Schulsinger et al. | |
| 6,160,084 A | 12/2000 | Langer et al. | |
| 6,322,553 B1 | 11/2001 | Vito | |
| 2003/0065247 A1 | * 4/2003 | Yap et al. ...................... 600/36 |
| 2003/0097040 A1 | 5/2003 | Clerin et al. | |

FOREIGN PATENT DOCUMENTS

WO 99/42528 8/1999

OTHER PUBLICATIONS

Bergsma, et al., "Low Recurrence of Angina Pectoris After Coronary Artery Bypass Graft Surgery With Bilateral Internal Thoracic and Right Gastroepiploic Arteries," *Circulation* 97(24):2402–05 (1998).

(Continued)

Primary Examiner—Beverly M. Flanagan
(74) Attorney, Agent, or Firm—Sutherland Asbill & Brennan, LLP

(57) ABSTRACT

Devices and methods are provided for forming a vascular graft by axially distending a blood vessel to induce growth. In one embodiment, a device for distending a blood vessel of a human or animal is provided which comprises a stretching mechanism attachable directly to a blood vessel at at least two attachment positions thereon, and a means for operating the stretching mechanism to cause the blood vessel portion between said at least two attachment positions to be stretched axially. The distended portion can then be excised and used as a graft.

30 Claims, 13 Drawing Sheets

OTHER PUBLICATIONS

Birukov, et al., "Stretch Affects Phenotype and Proliferation of Vascular Smooth Muscle Cells," *Mol Cell Biochem.* 144(2): 131–39 (1995).

Cooley, "Coronary Bypass Grafting With Bilateral Internal Thoracic Arteries and the Right Gastroepiploic Artery" *Circulation* 97(24):2384–85 (1998).

Cohen, et al., "Acute Intraoperative Arterial Lengthening for Closure of Large Vascular Gaps," *Plastic and Reconstructive Surgery*, pp 463–68 (1992).

Conklin, B., "Viability of Porcine Common Carotid Arteries in a Novel Organ Culture System", *MS Thesis*, Georgia Institute of Technology, 1997.

Costa, et al., "Increased Elastin Synthesis by Cultured Bovine Aortic Smooth Muscle Cells Subjected to Repetitive Mechanical Stretching," *Faseb J.*, 5: A1609, 7191 (1991).

Fu, et al., "Biorheological Features of Some Soft Tissues Under a Surgical Tissue Expansion Procedure," Biorheological Study on Tissue Expansion, 34: 281–93 (1997).

Han, et al., "Axial Stretch Increases Cell Proliferation in Arteries in Organ Culture", *Advances in Bioengineering, ASME, BED* 48:63–64 (2000).

Ippolito, et al., "Histology and Ultrastructure of Arteries, Veins, and Peripheral Nerves During Limb Lengthening," *Clinical Orthopaedics and Related Research*, 308: 54–63 (1994).

Kanda, et al., "Phenotypic Reversion of Smooth Muscle Cells in Hybrid Vascular Prostheses," *Cell Transplantation* 4(6):587–95 (1995).

Kolpakov, et al., "Effect of Mechanical Forces on Growth and Matrix Protein Synthesis in the In Vitro Pulmonary Artery," *Circulation Research*, 77: 823–31 (1995).

Leung et al., "Cyclic Stretching Stimulates Synthesis of Matrix Components by Arterial Smooth Muscle Cells in Vitro," *Science* 191:475–77 (1976).

Moore, et al., "A Device for Subjecting Vascular Endothelial Cells to Both Fluid Shear Stress and Circumferential Cyclic Stretch," *Annals of Biomedical Engineering*, 22: 416–22 (1994).

Ruiz–Razura, et al., "Clinical Applications of Acute Intraoperative Arterial Elongation," *J. Reconstructive Microsurgery*, 9: 335–40 (1993).

Ruiz–Razura, et al., "Acute Intraoperative Arterial Elongation: Histologic, Morphologic, and Vascular Reactivity Studies," *J. Reconstructive Microsurgery*, 10(6):367–73 (1994).

Ruiz–Razura, et al., "Tissue Expanders in Microvascular Surgery Acute Intraoperative Arterial Elongation," *Surgical Forum*, pp. 610–614 (1989).

Stark, et al., "Rapid Elongation of Arteries and Veins in Rats with a Tissue Expander," Plastic & Reconstructive Surgery, 80(4):570–78 (1987).

U.S. Appl. No. 09/994,241, filed Nov. 27, 2001, Vito et al.

* cited by examiner

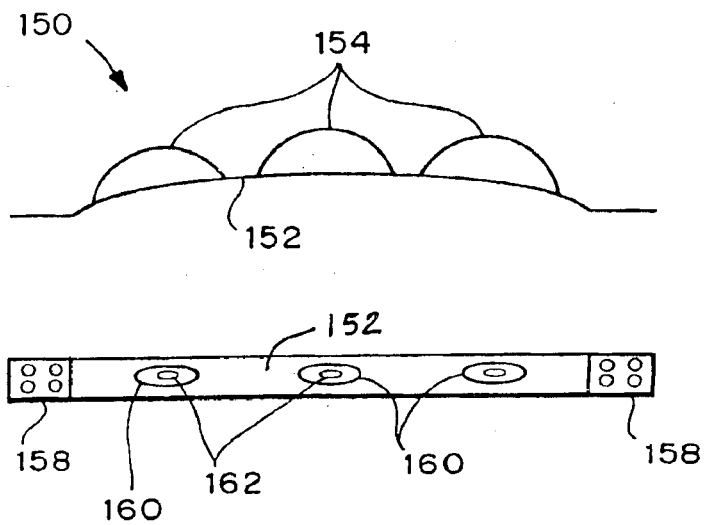
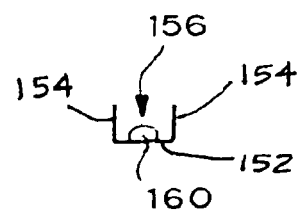
FIG. 7B
FIG. 7C
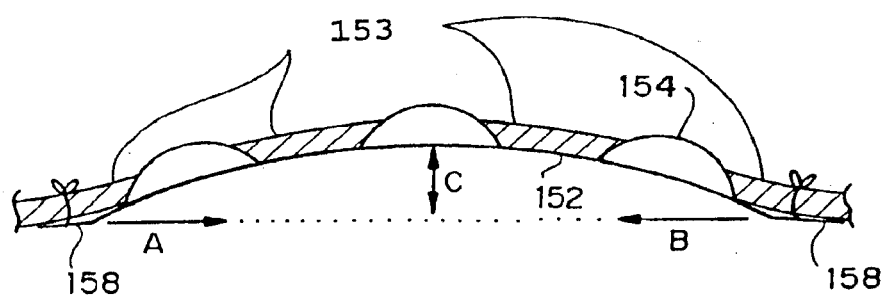
FIG. 8A
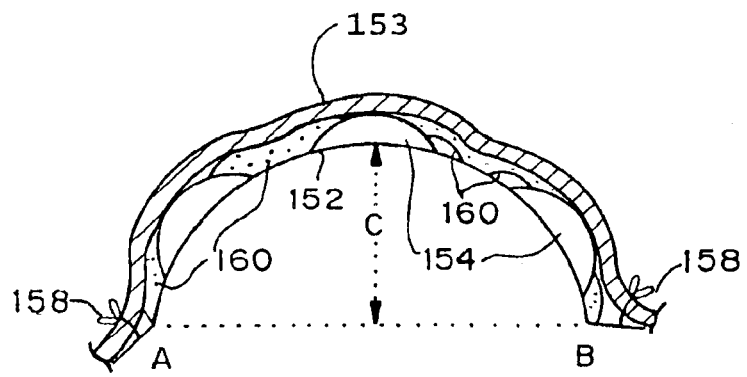
FIG. 8B

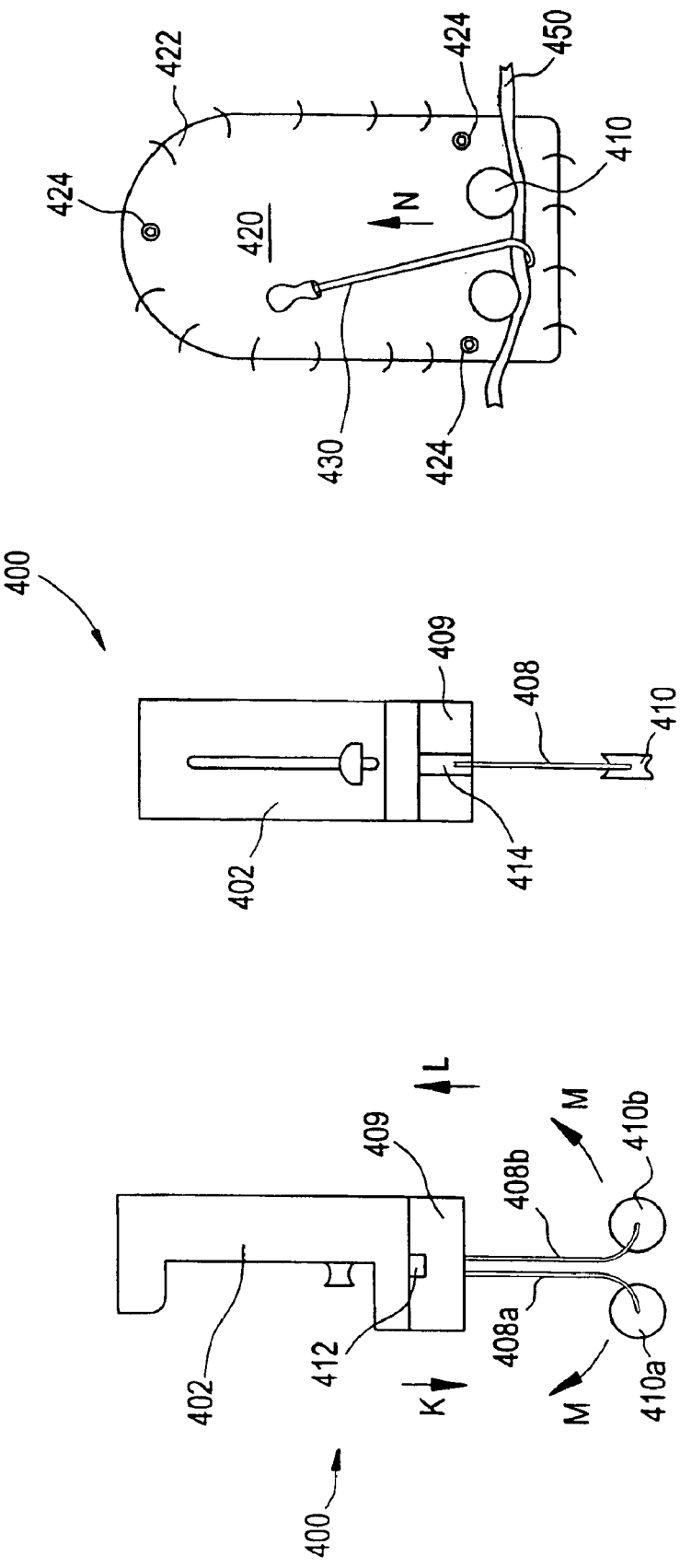

AUTOLOGOUS VASCULAR GRAFTS CREATED BY VESSEL DISTENSION

CROSS-REFERENCE TO RELATED APPLICATIONS

This is a continuation of U.S. application Ser. No. 09/994,241, filed Nov. 27, 2001, now U.S. Pat. No. 6,663,617, which is a continuation-in-part of application Ser. No. 09/322,095, filed May 28, 1999, now U.S. Pat. No. 6,322,553. Application Ser. No. 09/994,241 claims benefit of U.S. Provisional Application No. 60/274,909, filed Mar. 9, 2001, and application Ser. No. 09/322,095 claims benefit of U.S. Provisional Application No. 60/087,027, filed May 28, 1998. All of these applications are incorporated herein by reference in their entirety.

BACKGROUND OF THE INVENTION

The present invention is generally in the area of methods and devices to obtain vascular tissue grafts and more specifically in the area of methods and devices to obtain grafts, preferably autologous grafts, prepared from living vascular tissue.

Vascular grafts are commonly used by surgeons to bypass obstructions to blood flow caused by the presence of atherosclerotic plaques. Vascular grafts also are used in other applications such as providing arterial-venous shunts in dialysis patients, vascular repair or replacement and treating aneurysms. Grafts for bypass are often, but not exclusively, used in the coronary arteries, the arteries that supply blood to the heart. The materials used to construct a vascular graft usually are either synthetic or of biological origin, but combinations of synthetic and biological materials are under development. The most widely used biological vascular grafts are autologous saphenous vein or mammary artery. Some common synthetic grafts are made of polytetrafluoroethylene (PTFE) (e.g., GORTEX™) or polyester (e.g., DACRON™). Autologous grafts have generally been used more successfully than synthetic grafts. Autologous grafts remain patent (functional) much longer than synthetic grafts, and saphenous veins often fail in less than five years. The short lifetime of synthetic grafts is especially evident with small diameter (less than 7 mm diameter) grafts, as most small diameter synthetic grafts occlude within one to two years or less.

Small diameter vascular grafts are particularly used in coronary artery bypass surgery. Internal mammary artery (IMA) is the autologous graft of choice, because it typically has a longer life than venous grafts (95% patent at 5 years versus 85% patent at 2 years). Mammary arterial tissue, however, is difficult to harvest, typically is not available in lengths sufficient for multiple bypasses, and its removal can result in problems such as problematic wound healing. Moreover, obtaining sufficient venous tissue for repairing an occluded artery can be problematic in patients with venous conditions such as varicose veins and especially in second or third surgeries in the same patient. Recent literature also suggests that IMA used in bypass procedures either fails soon after transplantation or remains patent indefinitely. See, e.g., Bergsma, et al., *Circulation* 97(24):2402–05 (1998); Cooley, *Circulation* 97(24):2384–85 (1998). Other arteries such as the gastroepipolic, gastric, radial, and splenic also are used in coronary bypass procedures. Moreover, the recent American Heart Association/American College of Cardiology consensus document (Eagle, K. A., et al. "ACC/AHA Guidelines for coronary artery bypass graft surgery: A report of the American College of Cardiology/American Heart Association Task Force on Practice Guidelines", Committee to Revise the 1991 Guidelines for Coronary Artery Bypass Graft Surgery, American College of Cardiology/American Heart Association, *J. Am. Coll. Cardiol.*, 34(4):1262–347 (1999)) strongly recommends a move to total arterial revascularization.

In some cases, autologous or homologous saphenous vein preserved by freezing or other processes is used.

With people living longer, multiple surgeries are more common. At the same time, open-heart surgery is becoming routine, aided by the development of new, minimally invasive and "off-pump" procedures that have dramatically simplified the surgery and reduced the recovery time.

Development of a longer lasting small-diameter vascular graft is the subject of much academic and industrial research. One current approach is to combine cell culture and biomaterials technologies to make a living, "tissue engineered" graft. This effort, however, is hindered by the requirements of a successful graft: It should be self-repairing, non-immunogenic, non-toxic, and non-thrombogenic. The graft also should have a compliance comparable to the artery being repaired, be easily sutured by a surgeon, and not require any special techniques or handling procedures. Grafts having these characteristics are difficult to achieve. Despite the substantial effort to date and the potential for significant financial reward, academic and industrial investigators have failed to produce graft materials that have demonstrated efficacy in human testing.

Efforts to avoid or minimize the need for vascular grafts for repair of otherwise healthy vascular tissue have been described. For example, Ruiz-Razura et al., *J. Reconstructive Microsurgery*, 10(6):367–73 (1994) and Stark et al., *Plastic and Reconstructive Surgery*, 80(4):570–78 (1987) disclose the use of a round microvascular tissue expander for acute arterial elongation to examine the effects on the tissue of such acute hyperextension. The expander is a silicone balloon that is placed under the vessel to be elongated. The balloon is filled with saline over a very short period, causing acute stretching and elongation of the vessel. The method is purported to be effective for closure of arterial defects up to 30 mm without the need for a vein graft. These techniques are appropriate for trauma, but are not used for restoring blood flow in vessels that are occluded, for example by disease, which are treated by surgically bypassing the obstruction with a graft. The disclosed methods and devices fail to provide an autologous graft or versatile substitute. Moreover, the acute stretching may damage the vessel.

It is therefore an object of the present invention to provide devices and methods for creating natural blood vessel suitable for grafting.

It is another object of the present invention to provide devices and methods for making an autologous blood vessel graft.

It is further object of the present invention to provide devices and methods for creating blood vessel grafts in vivo or in vitro.

These and other objects, features, and advantages of the present invention will become apparent upon review of the following detailed description of the invention taken in conjunction with the drawings and the appended claims.

SUMMARY OF THE INVENTION

Devices and methods are provided for forming a vascular graft by axially distending a blood vessel to stimulate vessel growth. Preferably, the device is implanted, for example using endoscopic techniques, for use in vivo. A portion of a blood vessel (i.e., the donor vessel) then is distended using the device. Preferred donor vessels include the gastroepipolic artery, as well as the internal mammary, femoral, splenic, and radial arteries. Then, the in vivo distended portion of the donor vessel is excised, for example, at the time of bypass surgery. In an alternative embodiment, a section of donor vessel is surgically excised from the bypass surgery patient and then distended in vitro in a medium for cell growth, e.g., in an organ culture system or bioreactor. Where the donor is the recipient of the graft, the result using either approach advantageously is a totally autologous, living vascular graft.

In a preferred embodiment, the device comprises a stretching mechanism which includes (i) a rigid body; (ii) a pair of posts comprising a first post and a second post which are connected to the body; (iii) a driver element slidably secured to the body and disposed between the pair of posts; and (iv) a means for sliding the driver element away from the pair of posts to axially distend a blood vessel positioned between the pair of posts and the driver element. The posts of the device preferably have a curved lateral surface having a radius of curvature large enough to avoid collapsing the blood vessel during stretching In one variation, the body comprises a plate from which a pair of posts protrudes. This device may further include a second plate secured to the body defining a space in which the blood vessel is stretched. The posts can be integral with or attached to the base plate. In one embodiment, the posts are rotatably attached to the base plate.

In a more preferred, "foldable," variation, the body comprises a pair of movable arms connecting the pair of posts to the body. The arms can be oriented with the length of the body to provide a narrow device profile to facilitate in vivo insertion, and then once implanted can be deployed into a second position, suitable for blood vessel loading and stretching, approximately perpendicular to the longitudinal axis of the body. In this embodiment, the pair of moveable arms comprises a first arm and a second arm, each having a distal end and a proximal end, such that the proximal ends are hingedly connected to the body. The posts preferably are wheels rotatably attached to the distal end of each arm. Preferably, the body comprises a lower end portion that is adjustable to lock the moveable arms into two or more positions. The lower end portion can be biased by a spring to hold the lower end portion in engagement with the body.

The device typically includes a controller for controlling the means for sliding the driver element, in a continuous, intermittent, or cyclic manner. Preferably, the means for sliding the driver element comprises a prime mover that is mechanically, electromechanically, or hydraulically driven. In one embodiment, the device further comprises a guide rod, which passes through an aperture in the driver element to guide the movement of the driver element as the driver element is slid along the guide rod by the means for sliding. Other mechanisms for imparting lateral stability to the driver element include the use of a protrusion or groove that matingly engages with a corresponding groove in or protrusion from the body to guide the movement of the driver element as the driver element is slid by the means for sliding.

The means for sliding the driver element can include one or more springs. These springs can provide constant stretch or a nonlinear or a constant force-deformation response. In one embodiment, the spring can comprise a shape memory material so the spring's stiffness or shape can be changed as stretching progresses or periodically.

The device optionally can include a growth factor or other growth stimulating agent for release in an effective amount to enhance growth of the blood vessel. Such agents may be impregnated into the materials of construction forming the device or can be in the form of a coating or a reservoir device attached to the stretching device.

BRIEF DESCRIPTION OF THE DRAWINGS

FIGS. 7A–C are front (7A), plan (7B), and side (7C) views of one embodiment of a device for both rectilinear and curvilinear vessel distension.

FIGS. 8A–B are diagrams showing vessel distension using one embodiment of the device for both rectilinear and curvilinear vessel distension.

FIGS. 20A–B illustrate the device of FIG. 19 with the moveable arms and posts in a folded or undeployed position.

FIG. 21 is a plan view of one embodiment of a bottom plate for isolating the stretching device for surrounding tissue and securing the device in place in vivo.

DETAILED DESCRIPTION OF THE INVENTION

Figure 1:
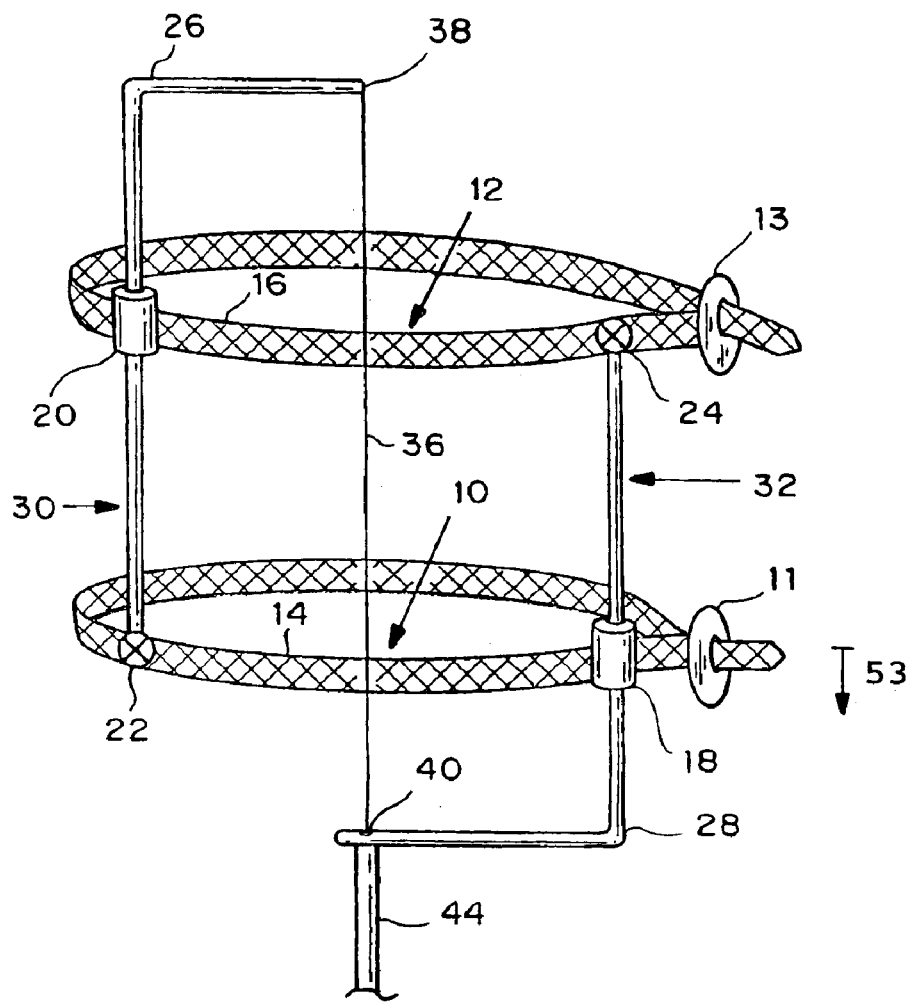
FIG. 1 is a plan view of one embodiment of the device for vessel distension.
Figure 1:
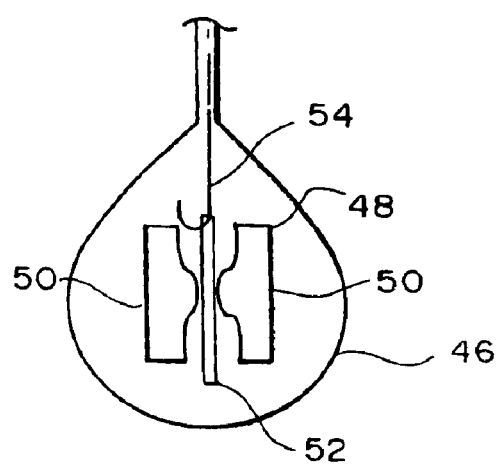

It is known that smooth muscle cells, which dominate the media, the major load bearing layer of the arterial wall, proliferate and increase their production of extracellular matrix in response to mechanical stimulation. It was discovered that this knowledge could be advantageously applied to create an autologous graft of appropriate diameter for coronary bypass or other vascular graft application using a distension device to stimulate angiogenesis. While an autologous graft is preferred, the devices and methods described herein also can be applied to an artery from another human or other animal, including transgenic animals genetically engineered to have tissues that will not be rejected by humans. The distension device can be adapted to operate in vivo or in vitro.

The devices and methods described herein can used to make allogeneic and xenogeneic vascular grafts, as well as the more preferred autogeneic vascular grafts.

Distension Device

The distension device secures the donor blood vessel at different points on the vessel and then distends or stretches the vessel between those points to form an elongated portion. The elongated portion can then be excised for use as a vascular graft. Stretching can be continuous, cyclical, or intermittent, and can occur rectilinearly, curvilinearly, or in a combination thereof. The stretching can occur between vessel attachment points that are movable relative to one other or in fixed positions relative to one other.

I. Movable Attachment Positions

The device typically includes a stretching mechanism that can be attached by means such as straps or sutures to the donor blood vessel, a means for operating the stretching mechanism to cause the vessel to distend (i.e., extend), and a controller for controlling the operating means.

A. Stretching Mechanism

In a preferred embodiment, the distension device stretching mechanism includes a pair of opposed straps or loops that are fixedly attached to the donor blood vessel such as by sutures. The opposed straps are displaced away from each other over a period of time so that the donor vessel elongates as the straps are displaced. After a period of time, such as when the straps are displaced a pre-determined distance, the section of vessel and the device are removed and the ends of the donor vessel are sutured together if needed.

The device straps should be made out of a biocompatible material such as a synthetic or natural polymer or metal. The straps must be able to be attached to the vessel, for example, using sutures, staples, or adhesion. Examples of suitable material for the straps are polytetrafluoroethylene (PTFE), polyester (e.g., DACRON™), nylon (e.g., DELRIN™), polysulfone, polypropylene, and polyethylene. The strap material preferably is doped to render it radio opaque, so that the stretching process can be monitored using x-ray techniques. The straps can be wrapped in a material that is then attached to the vessel, or they can include perforations or holes to accommodate suturing to the vessel. The straps preferably have a flex strength to support the distending force applied on the stretching mechanism.

The device includes a means to displace the straps away from each other and stretch the vessel. This displacement can be accomplished by any of a variety of techniques. For example, the device can include rods attached to the straps that can be moved to push or pull on the straps to slowly displace the straps from each other. The rods can be moved, for example, by mechanical or hydraulic means.

B. Operating Means

The device includes means to operate the stretching mechanism, preferably including a prime mover and electronic drivers for the prime mover, both of which are preferably implanted. The prime mover can be an electromechanical (active) device, such as a linear motor that operates the stretching mechanism to push and/or pull the straps away from each other. A rotary motor could also be used to generate the required linear motion, using techniques known in the art. Alternatively, the prime mover can operate hydraulically. An active device generally requires input over time. The prime mover also can be a passive device such as a spring or a combination of a spring and a damper, where stored mechanical energy is used to push and/or pull the straps away from each other.

Linear or rotary piezo micro-motor devices (actuators) deliver small step sizes, small forces, have relatively simple control electronics and inherent force overload protection. Suitable devices are available from a number of vendors, including Micro Pulse Systems, Inc. Parameters of the operating means include the force applied by the stretching mechanism, the rate and direction of movement of the stretching mechanism, the length of time that the stretching mechanism is operated, and the type of stretching applied (e.g., continuous, cyclical, or intermittent).

C. Controller

The controller controls the operating means. In the in vivo distension embodiments, the controller can include a microprocessor that is implanted and that can be activated, programmed, or reprogrammed by an externally applied magnetic or electromagnetic field. The controller also can be activated, programmed, or reprogrammed externally using wires that pass through the skin, or by wireless means for transmitting power or data known in the art wherein wires need not pass through the skin.

One embodiment of the device is shown in FIG. 1. Proximal locking strap 10 and distal locking strap 12 are of adjustable length appropriate for a secure fit around the donor blood vessel to be distended. Blood vessels range from about 0.2 to 2 cm in diameter. The locking straps 10, 12, include a lace 14, 16, respectively, of a biocompatible material, such as DACRON™, that can be secured to the donor vessel, such as by suturing, stapling, or using an adhesive agent. In a preferred embodiment, the laces are designed similarly to the sewing rings of a standard artificial heart valve. Alternatively, a layer of a material, such as a fabric or film, can be attached to the strap so that the vessel can be sutured, stapled, or adhered to the material to hold the strap to the vessel. In another embodiment, the strap includes perforations, holes, or other structural features amenable to suturing or stapling, so that the vessel can be sutured or stapled directly to the strap. The locking straps each have a head 11, 13 with an internal aperture. Preferably, the straps 10, 12 include a plurality of teeth (not shown) that, when the free end of the lace 14, 16 is inserted through the aperture of the head of the strap, it engages the head and prevents the free end of the lace from becoming disengaged, in a manner similar to that of standard pull-ties. Alternatively, the head of the strap can engage the strap if the lace 14, 16 does not cover the entire strap or if the strap includes securing holes or perforations as described above. The straps optionally may be impregnated or coated with one or more growth stimulating agents (e.g., growth factors) that can be released in an effective amount to promote vessel tissue growth during the stretching procedure.

Sliding bearings 18, 20, on straps 10, 12, respectively, and stops 22 and 24, respectively, can be either attached to or integrally formed (during manufacture) with the straps or laces as shown. The bearings and stops are preferably made of the same material as the straps, although other biocompatible materials can be used.

A first push/pull rod 26 is fixedly attached to proximal tie strap 10 at stop 22. A second push/pull rod 28 is fixedly attached to distal tie strap 12 at stop 24. The two push/pull rods are preferably initially not fitted to the locking straps but are easily assembled on the device in vivo after the locking straps are secured around the vessel and sutured or otherwise fixed in place. The push/pull rods slide through the bearings 18, 20 and engage the stops 22, 24. The proximal locking strap 10 including the lace 14, sliding bearing 18, stop 22, and the fixedly attached rod 26 form a first integrated stretch unit 30. The distal locking strap 12 including the lace 16, sliding bearing 20, stop 24, and the fixedly attached rod 28 form a second integrated stretch unit 32. Push/pull rods 26, 28 are preferably made of a rigid material such as stainless steel, titanium or a biocompatible, rigid plastic.

Figure 2:
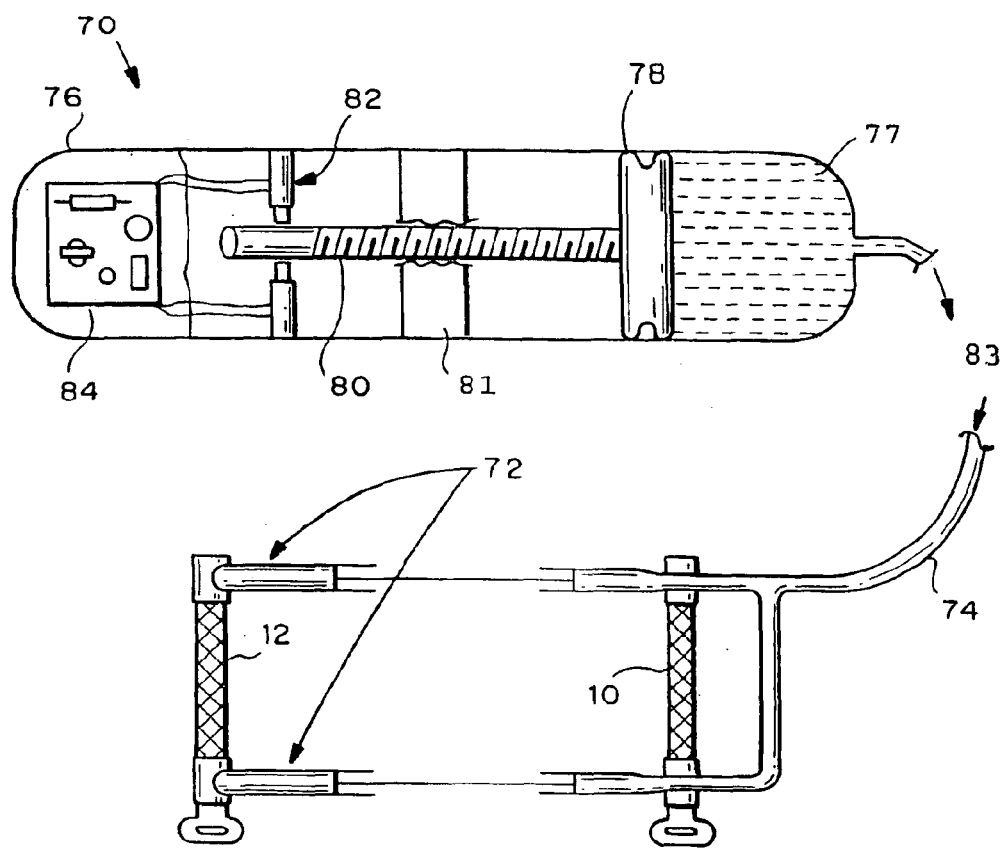
FIG. 2 is a plan view of a second embodiment of the device for vessel distension.

A wire (or cable) 36, preferably stainless steel or titanium, is fixedly attached to first push/pull rod 26 at 38 and passes freely through a hole 40 in push/pull rod 28. The wire 36 then passes freely through the sheath 44 into the prime mover housing 46. The prime mover shown is a piezo-actuator or other linear motor. Those skilled in the art will recognize that several suitable means for pulling the wire or cable are known. For example, the wire or cable can be pulled by a hydraulic cylinder or actuator powered by an implanted pump or by transcutaneous injection of a fluid, such as saline. The wire or cable also could be wound on a rotating reel or attached to a lead screw configured to produce linear motion, wherein either is powered by electric or hydraulic rotary actuators. FIGS. 1 and 2 show two opposing piezo-actuators 50 contained in the housing 46 which can be activated to provide micron-sized step advancement of the driven element 52. Wire 36 is attached to driven element 52 by a hook 54 or other means so that wire 36 is advanced along with driven element 52. Micro Pulse Systems, Inc. makes micro-actuators that are suitable for the device disclosed herein.

As the actuator 48 pulls the wire 36, the first integrated stretch unit 30 is pushed/pulled towards the actuator 48, in the direction of arrow 53. The locking straps are thus displaced away from each other.

The device preferably includes an external driver and controller, which are not shown in the Figures. In a preferred embodiment, the wire can be activated from outside the body once the wire is passed through the skin. Mechanisms outside the body are easier to design and transcutaneous catheters and similar conduits are highly developed.

Figure 9:
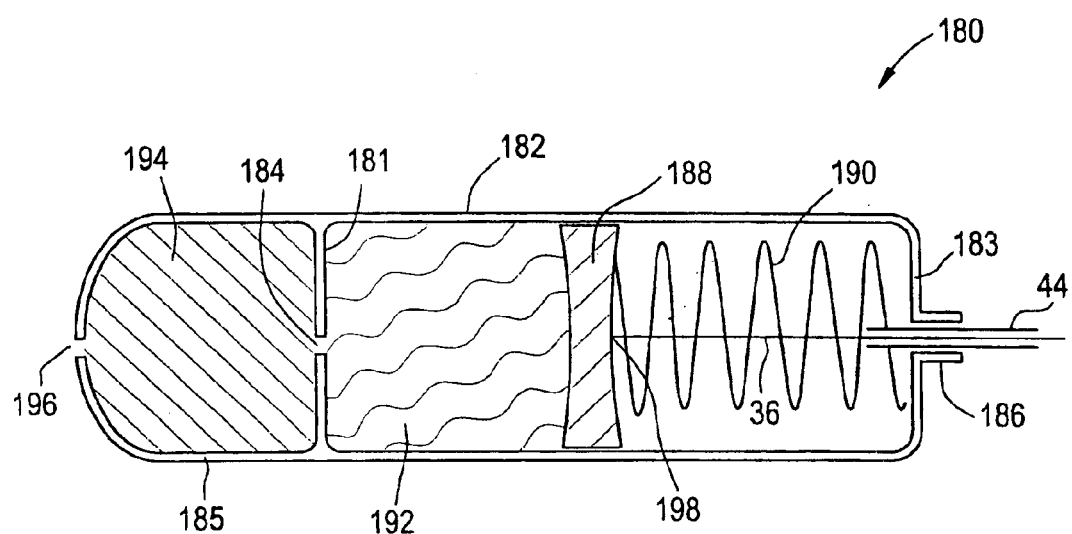
FIG. 9 illustrates a passive power source adaptable to powering the stretching device shown in FIG. 1.

A particularly simple passive device for producing the linear motion needed to pull the wire 36 is illustrated in FIG. 9. The device 180 includes a cylinder 182 having a first orifice 184 at one end 181 and a second orifice 186 at the other end 183, and containing a movable piston 188, a compression spring 190, and working fluid 192. Adjacent the one end 181 is an extension 185 of the cylinder 182, which contains an absorbent material 194 and includes a vent hole 196. The sheath 44 of wire 36 enters the cylinder through second orifice 186, and the wire 36 is attached to the piston 188 at its center 198. The spring 190, which typically is made of stainless steel, titanium or titanium alloy, particularly nickel-titanium, is in compression and pushes piston 188 toward first orifice 184, thereby forcing the fluid 192, typically a biocompatible saline solution, through first orifice 184, where it is absorbed by the absorbent material 194. Representative examples of absorbent materials include synthetic hydrophilic substances, such as certain polymers, or natural materials, such as cellulose. Air or other gas in the interstices of the highly absorbent material 194 that is displaced by the fluid 192 exits from the piston through vent 196. It can be seen that the piston movement provides a continuous driving force and linear motion to the wire or cable 36 in the embodiment shown in FIG. 1. The first orifice 184 can be of a fixed size or a variable size to control the movement of the piston 188. For example, orifices made of piezoelectric or magnetostrictive materials can be made to selectively vary in size by the application of an appropriate electric or magnetic field. The spring 190 can have a linear, nonlinear or constant force deflection characteristic and may consist of multiple springs acting together and designed to produce the required stretching force and motion profile. Those skilled in the art will recognize that this device can be adapted to either push or pull on the cable or wire, depending on the arrangement of the elements.

FIG. 2 illustrates a second embodiment 70 of a device for vessel distension. The hydraulic embodiment uses two miniature, double-acting hydraulic cylinders 72, for example made of stainless steel, titanium or polymer, through which hydraulic force is exerted to stretch the blood vessel by pushing on straps 10. Double acting hydraulic cylinders 72 are connected by a hydraulic line 74 into which fluid flows from the housing 76 which comprise a reservoir of a fluid 77 such as saline. Pressure is generated by a piston 78 driven by threaded rod 80, positioned on a rod support 81, pushing the saline from the reservoir out at 83. Alternatively, pressure may also be generated by means external to the body using a catheter through the skin or by injection into an implanted, subcutaneous port. Such ports are commonly available. The threaded rod 80 is driven using torque generated by frictional engagement with piezo-actuators 82 or by a miniature permanent magnet or other suitable motor. Micro Pulse Systems Inc. supplies piezo-actuators suitable for use in the device. Driver electronics and a power source are indicated as numeral 84. Note that while FIG. 2 shows a hydraulic mechanism wherein only strap 10 is moved, the hydraulic system may be readily adapted by one of skill in the art to exert force on both strap 10 and strap 12.

Alternatively, one skilled in the art could adapt the spring driven piston system illustrated in FIG. 9 to provide hydraulic power to the embodiment illustrated in FIG. 2.

The mechanical or hydraulic stretching mechanism works to move the straps apart slowly over a period of up to several weeks. In one embodiment, the passive driver element illustrated in FIG. 9 may be used to provide a predetermined stretch over time. In another embodiment, the driver may be pre-programmed to operate autonomously, or the driver may be programmed (or reprogrammed) following implantation by transcutaneous electromagnetic means, based, for example, on x-ray data or other indications of how the process is proceeding. The driver may be simply turned on or off, or may be programmed or reprogrammed by a magnetic field sensing device such as a reed switch (relay) or by other electronic devices or circuits responsive to magnetic or electromagnetic fields. The field is generated by using the external driver control to periodically activate an external source positioned to activate the electronic driver circuit. The external driver control may be pre-programmed to provide a stretch of several centimeters over about one month. Alternatively, cyclic stretching of increasing peak and mean amplitude may be used. Using piezo actuators, activating the driver can produce incremental movements of the mechanical or hydraulic stretching mechanism as small as a few microns. The prime mover is designed to be force limited to preclude overstretching the vessel. Force limitation is inherent if the piezoelectric actuators are used in either embodiment and, in the case of permanent magnetic motors, can be designed into the electronic driver circuit.

II. Fixed Attachment Positions

Figure 4A:
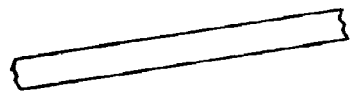
FIGS. 4A and 4B are illustrations of a normal and stretched blood vessel.
Figure 4B:
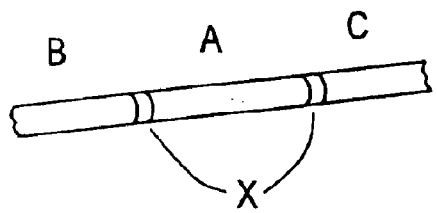

In stretching an artery to stimulate angiogenesis, the blood vessel portion that is beyond the region where the stretching apparatus is attached will be relaxed from its normal stretched state and could possibly be relaxed to the point where it is put in compression, as illustrated in the FIGS. 4A and 4B. FIG. 4A illustrates a blood vessel as it is normally stretched in vivo, and FIG. 4B illustrates how a stretching device having points of contact (X) between vessel sections A and B and between A and C. The stretching device elongates section A while relaxing sections B and C. The consequences of this are unknown, but can be avoided if the blood vessel is stretched between two fixed points, as described herein.

Figure 5A:
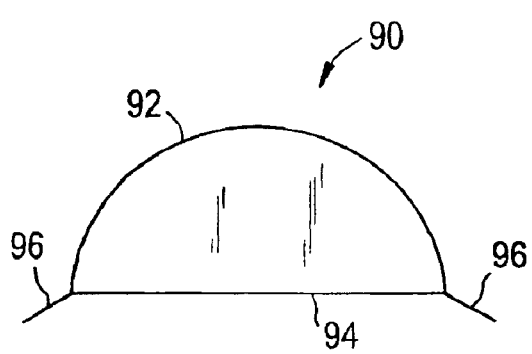
FIGS. 5A–C are front (5A), plan (5B), and side (5C) views of one embodiment of the device for vessel distension using fixed points of vessel attachment.
Figure 5C:
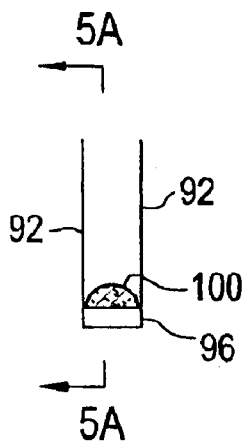
Figure 5B:
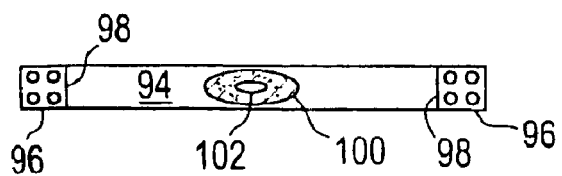

One embodiment of the fixed-point device is shown in FIGS. 5A–C. The device 90 includes two semicircular or similarly shaped thin, yet rigid, plates 92 made of or completely covered by a biocompatible material, such as stainless steel, titanium, titanium alloy, fiber composite, or polymer. The plates are separated and connected so as to remain parallel by a flat rectangular strip of similar material 94. The ends of the strip 96 are perforated or otherwise formed to accept surgical sutures or other means (e.g., adhesive) known in the art to secure a blood vessel to the strip at its ends. The ends 96 are also flexible and easily bent, but without breaking, about axis 98 shown. The device can be formed from a single appropriately shaped thin plate. The area between the plates contains at least one inflatable balloon 100, which may be formed from silicone, rubber, elastomeric polymers, or any other highly deformable biocompatible material. As the balloon 100 is inflated, it fills the space between the two thin plates 92 without significantly changing the spacing between the two plates 92, since the plates 92 and strip 94 are sufficiently rigid to ensure this. Inflation of the balloon 100 can be accomplished using at least one access port 102, through which a fluid, such as saline, is injected, for example, through a needle or catheter connected to a syringe or similarly functioning device. The inflation process can occur through the skin. The balloon is designed and attached to the strip in such a manner that, at full inflation, it assumes more or less the shape of the space between the two plates confining it.

An alternative stretching mechanism is provided by hydrophilic or chemically reactive synthetic substances (e.g., various polymers) or other natural materials (e.g., cellulose) known to significantly expand their dry volume when activated as by exposure to fluid or possibly other stimuli (e.g., heat, radiation or various chemical agents). Such materials are available in foamed, fiber or other forms, any of which may be adapted by one of skill in the art to effect the balloon inflation described herein. One or more of these materials can be placed inside the balloon and expanded by the controlled addition of a fluid or chemical agent, such as by injection into the balloon, which causes the materials to expand, inflating the balloon, in much the same way as simply pumping saline or another fluid into the balloon as described above. The material could also be otherwise encapsulated or separated from the stimuli to control its means and rate of activation. For example, expandable material could be provided with a degradable coating or other timed-release mechanism, and such mechanisms can be readily adapted from those used in controlled drug delivery. Alternatively, the balloon can be omitted, and the hydrophilic or other volume expanding material can simply be placed between the two plates in such a manner that exposure to body fluids or another appropriate stimulus causes the material to expand and fill the area between plates.

III. Combination Fixed/Movable Attachment Positions

Other embodiments combine rectilinear and curvilinear stretching. One such embodiment is a slightly modified version of device 90 (shown in FIGS. 5A–C) and is illustrated in FIGS. 7A–C. The device 150 includes strip 152, that is formed much like strip 94, except that it is formed in a slightly curved or angled configuration and includes at least one, and preferably several, plates (or tabs) 154, positioned at or near the long edge of the strip 152 so as to form a channel 156. Strip 152 has flexible ends 158 for attachment to the blood vessel. A blood vessel is placed in channel 156 and attached to the strip 152, like described for strip 94, wherein plates 154 serve to hold the blood vessel in place. The space between the plates contains one or more (three are shown) inflatable balloons 160, which are like balloon 100 described above. Inflation of the balloon(s) can be accomplished using at least one access port 162, also as described above.

Method for Distending a Blood Vessel

The distension device can be adapted to operate in vivo or in vitro, that is to distend a portion of a blood vessel in vivo or following its excision from the body and subsequent placement in a medium for cell growth. As used herein, the phrase "medium for cell growth" includes any in vitro system for facilitating cell division, extra-cellular matrix formation, and growth of vessel tissue. For example, the distension device can be attached to an excised portion of donor vessel and submerged in a medium for cell growth in a temperature-controlled container. As described in Example 1, it has been shown that distension in an organ culture (e.g., a bioreactor) significantly stimulates cell division, and can be simple to control. See, for example, U.S. Pat. No. 5,899,936 to Goldstein; U.S. Pat. No. 5,879,875, to Wiggins, et al.; and U.S. Pat. No. 5,888,720 to Mitrani, which describe techniques for organ and tissue culture which can be adapted to the methods described herein.

I. Operating the Movable Positions Device

The method for distending a donor blood vessel can include attaching a stretching mechanism to the donor vessel and operating the stretching mechanism to stretch the donor vessel. In one embodiment, the method involves using a device wherein a pair of straps are fixedly attached to the donor vessel and moved away from one another so that the portion of the vessel between the straps is distended. The distended portion can then be excised and used as a graft. Grafts for coronary by-pass surgery are typically between about 10 cm and 15 cm in length, whereas grafts for by-pass in the peripheral circulation are typically about 25 cm or more in length. Those of skill in the art can readily optimize the rate of vessel distension. Distension rates can be linear or nonlinear, and may average, for example, between about 5 and 10 mm/day.

Figure 3:
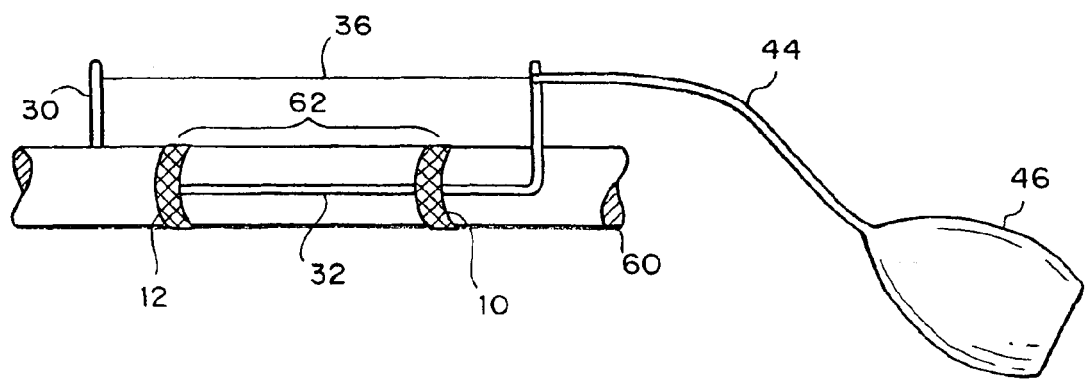
FIG. 3 is a side elevational view of the distension device shown attached to a donor blood vessel.

One embodiment of the method is illustrated in FIG. 3, wherein a device (e.g., the one shown in FIG. 1) is attached to a donor blood vessel 60. The device can be assembled before or at the time of implantation. Straps 10, 12 are engaged to encircle the donor vessel and are then sutured in place. Push/pull rods 30, 32 are attached to the straps. Wire 36, and the housing assembly shaft 44, and housing 46

(containing the actuator) are attached to the device. Preferably, the active prime mover is implanted complete with its drive circuit and a minimal power source. Alternatively, a passive device, such as described above, can be used. As either device is operated, the section of vessel 60 between the straps 10, 12, indicated by 62, stretches.

II. Operating the Fixed Positions Device

Figure 6A:
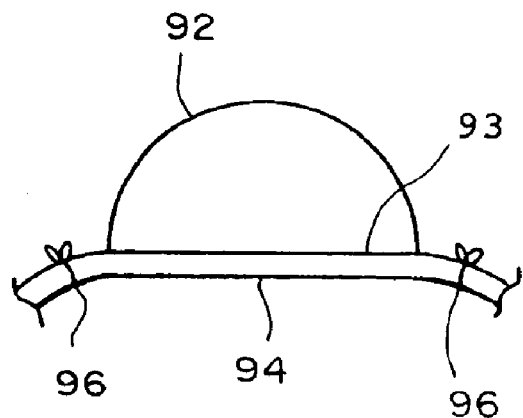
FIGS. 6A–C are diagrams showing vessel distension using an embodiment of the device having points of vessel attachment that are fixed relative to one another.
Figure 6B:
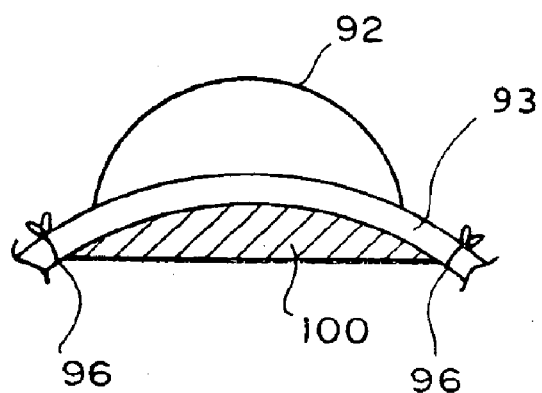
Figure 6C:
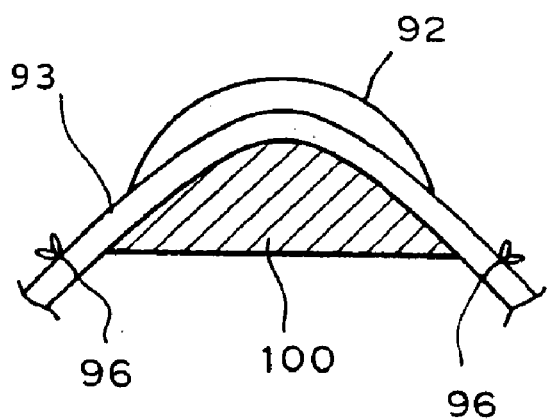

The device using fixed attachment positions is preferably operated as shown in FIGS. 6A–C, which show a cross-sectional view (a—a) of the device in FIGS. 5A–C, at increasing degrees of vessel distention occurring with increasing inflation/expansion of the balloon/expanding material. In operation, the target blood vessel 93 is placed between the two plates 92, resting on the uninflated balloon 100 (or unexpanded material) and secured to the flexible ends 96 of the strip 94, for example by sutures or other suitable means (FIG. 6A). As the balloon is inflated (or the material expanded), the blood vessel 93 is stretched (FIG. 6B), between the two fixed ends 96 and continues to stretch as the space between the two plates is filled (FIG. 6C), without the possibility of reducing the tension in or compressing the blood vessel 93 not between the points of attachment.

III. Operating the Combination Fixed/Movable Positions Device

The device using the combination of fixed and movable attachment positions is preferably operated as shown in FIGS. 8A–B. FIG. 8A shows a blood vessel attached to the device before application of the bending force (i.e., before distension). FIG. 8B shows the device and blood vessel following application of the bending force, wherein strip end A is drawn towards strip end B. The device can be, for example, device 150 described above.

In operation, the target blood vessel 153 is first placed in the channel formed by plates 154, resting on the uninflated balloon 160 and secured to the flexible ends 158 of the strip 152, for example by sutures or other suitable means. The ends 158 of the strip 152 are then drawn towards each other by mechanical or other forces to cause strip 152 to bend or flex, thereby stretching the blood vessel 153. The ends can be drawn towards one another by any suitable means, including a mechanical or magnetic force, or by a differential expansion effect, for example where the strip consists of laminates of materials that contract or expand differently from one another when exposed to a stimulus, such as heat (thermal expansion) or water (e.g., top layer of strip hydrophilic while bottom layer hydrophobic). The mechanical means can include, for example, the linear or rotary piezo micro-motor devices described herein. As the strip 152 is bent, distance C increases and distance AB decreases, causing the section beyond either A or B to be stretched in a rectilinear manner.

Additionally, as balloon 160 is inflated (or the material expanded), the blood vessel is stretched between the two ends 158 and continues to stretch as the space in the channel defined by plates 154 is filled. Thus, the section of blood vessel between ends A and B is stretched in a curvilinear manner. The two modes of stretching can occur simultaneously, one after another in either order, or any combination thereof.

IV. In Vitro Operation

Currently, a short segment of blood vessel can be salvaged during conventional bypass surgery and an in vitro organ culture or bioreactor system can be used to grow sufficient graft tissue for a second surgery. Such surgeries represent about 30% of all bypass operations. The methods and devices described herein can be adapted to work with such surgeries, to increase the length of graft material and/or to reduce the required length of the salvaged segment. Stretched blood vessels can be effectively preserved for bypass surgery, for example, using known cryogenic or freeze-drying techniques.

Application of the Distension Devices and Methods

The present devices and methods are useful for forming a vascular graft by axially stretching (i.e., distending or extending) a donor blood vessel to stimulate growth. This stretching can performed in vivo or in vitro.

The devices and methods can be sized to stretch blood vessels of essentially any size and located in or excised from a variety of sites in the body of the patient or donor or animal. Preferred blood vessels include, but are not limited to, the internal mammary arteries, the gastroepipolic artery, the gastric artery, the radial artery, the femoral artery, and the splenic artery. Other arteries and veins may also be suitable blood vessels for use with the methods and devices.

In a preferred embodiment of the in vivo distension method, the device is implanted, for example using endoscopic techniques, in the patient and vessel distension effected over a period of time. Then the site of implantation is re-exposed, all or a portion of the donor blood vessel section (e.g., vessel segment 62 in FIG. 3) is removed and the device is explanted. The ends of the donor vessel can then be sutured end to end to repair the donor vessel, as is commonly done in vascular repair without complication. Some blood vessels used for coronary bypass surgery, such as the gastroepipolic and radial arteries, can be removed with minimal morbidity such that repair is unnecessary. The removed blood vessel section is then ready for use as a graft in a patient in need thereof, who preferably is the same patient supplying the donor vessel.

In a preferred embodiment of the in vitro distension method, a portion of donor blood vessel (e.g., shorter than that needed for a graft) is surgically excised from the patient in need of the graft, and then the vessel portion is stretched over a period of time in vitro in a medium for cell growth, for example, as in a bioreactor. All or a portion of the distended vessel is then ready for use as a graft in the patient. Where the donor is the recipient of the graft, the result using either approach advantageously is a totally autologous, living vascular graft.

Preferred Embodiments

In a preferred embodiment of the device, the stretching mechanism is not actually attached to the blood vessel and is therefore easier to use, as no suturing of the device to the vessel is required. The device also preferably is enclosed so that the possibility of tissue adhesions to soft tissue and/or infiltration by body fluids—potential problems with essentially any implanted device—is minimized. The device also preferably includes growth factor to stimulate blood vessel tissue growth. For in vivo applications, the device also preferably is sized and shaped to facilitate minimally invasive implantation, such as by endoscopic insertion.

In preferred embodiments, a driver element is used to stretch a blood vessel positioned between two fixed posts. Generally, the devices can be designed to have a fixed outer shape or, more preferably, to "fold" to yield a reduced profile to facilitate insertion (i.e., implantation).

In all of these preferred embodiments and variations, the body preferably is a substantially rigid, elongated structure. The devices are designed so that their cross-sectional dimensions facilitate endoscopic implantation, preferably using available hardware. Standard trocars for endoscopic access range in size to 25 mm. Device length is influenced by choice of artery, length of graft produced, and other factors. The expected length is between about 4 and 20 cm.

Non-Fold Design

In a preferred embodiment, the blood vessel lies between two parallel plates, in a configuration similar to the embodiment described above in FIGS. 5 and 6. The basic elements and operation of this embodiment of the device is shown in FIGS. 10 and 11 which illustrate device 200 in a partially exploded view.

The device 200 includes a base plate 202 and optional cover plate 204. The base plate 202 has a first surface 206 from which a pair of posts 208a and 208b extends. The posts 208a and 208b each have a lateral surface 209a and 209b, which preferably are shaped to accommodate or fit the circular cross-sectional shape of the blood vessel being stretched. As used herein, the term "post" includes any suitable member or structure attached or integral to the surface of the plate that has a surface capable of supporting the blood vessel during stretching of the vessel. The base plate 202 further includes a support member 214 that extends from the first surface 206.

Figure 10:
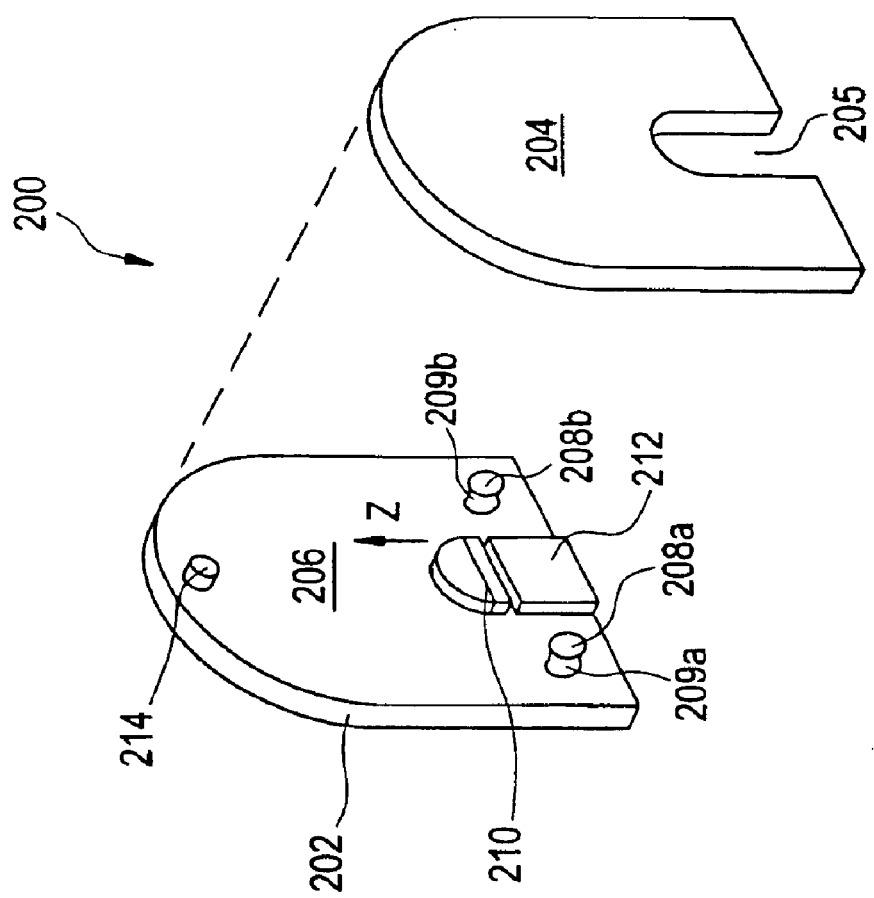
FIG. 10 is a perspective, partially exploded view of one preferred embodiment of a stretching device comprising a moveable driver element and fixed posts.

The base plate 202 further includes a moveable driver element 210 on the first surface 206, shown in FIG. 10 in its resting position on optional resting member 212, which in this embodiment is in the form of a rectangular protrusion. The driver element 210 is moveable along the first surface 206 in a direction away from resting member 212, preferably along a line perpendicular to a line between the center points of posts 208a and 208b, shown as arrow Z. The means for moving and controlling the movement of the driver element 210, which controls the stretching of the blood vessel, are described below.

The cover plate 204 includes a cutout area 205 that has the approximate size and shape of the combination of the driver element 210 and resting member 212. The cover plate 204, which preferably is flat, is made so that it may be secured to the base plate 202, preferably by being attached at the posts 208a and 208b and at support member 214. Essentially any suitable protrusion or other mechanism can be used for attaching the cover plate and the base plate together. For example, snap type connectors can be fabricated into the base plate and/or the cover plate. Such connectors are known and routinely used by those skilled in the art. Snap connectors are particularly well suited to structures made with biocompatible polymers, for example, in a molding process. Representative examples of such polymers include PTFE and DELRIN™ (E. I. du Pont de Nemours and Company) acetal polymer.

Figure 11A:
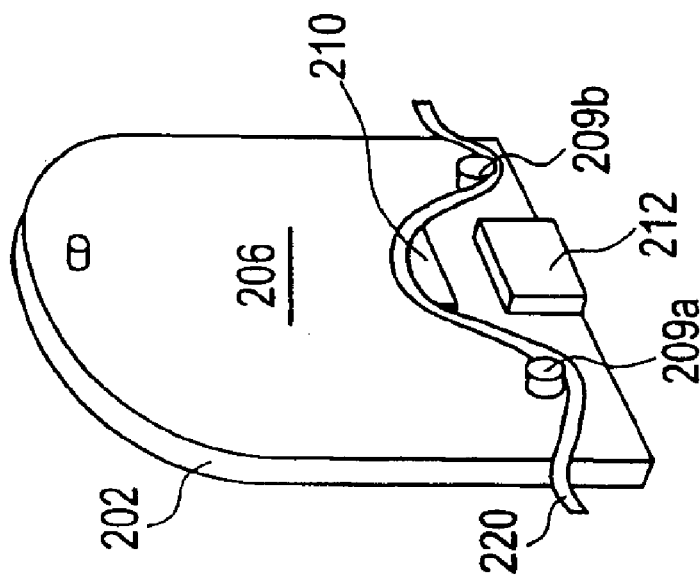
FIGS. 11A–B is a perspective view of the device in FIG. 10 in operation.
Figure 11B:
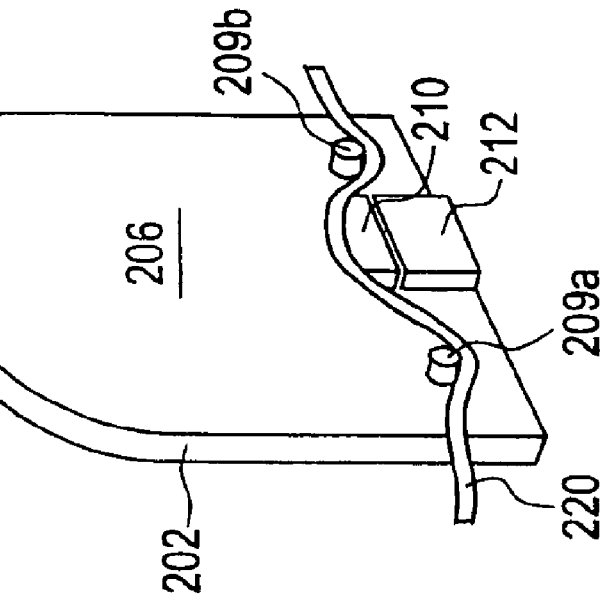

FIGS. 11A–B illustrate how device 200 operates to stretch and lengthen a blood vessel. (For clarity, the cover plate 204 is not shown.) FIG. 11A shows blood vessel 220 positioned (i.e., threaded) between posts 209a and 209b and driver element 210, which is in its initial position. To load the device, a length of blood vessel having a length approximately equal to the distance between the posts 209 is freed from the tissue tethering (that is commonly associated with mammalian arteries, for example) and then placed into the threaded position in the device. FIG. 11B shows the blood vessel 220 stretched by movement of the driver element 210, which has moved away from resting member 212.

It is desirable to make the stretching device as small as possible so that it may be delivered in vivo using standard or specially designed endoscopic tools. The elements of this embodiment can be fabricated using suitably rigid materials and known fabrication methods. Materials such as stainless steels, titanium, titanium alloys or biocompatible polymers are suitable. Methods for forming the elements of the device are well known to those skilled in the art.

Figure 12:
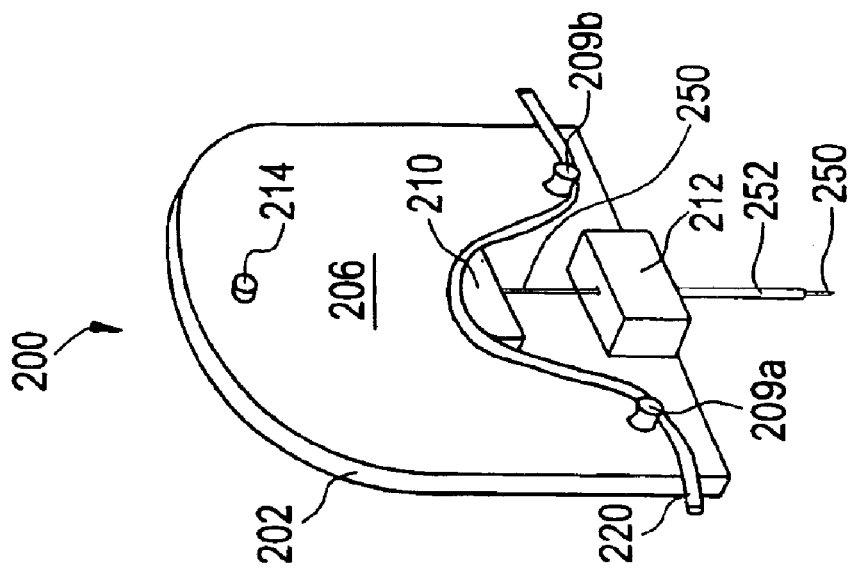
FIG. 12 is a perspective view of the device of FIG. 10 wherein the driver element is controlled by a push/pull wire.

The movement of the driver element can be controlled by a wide variety of means. In one embodiment, the driver element is moved by means of a wire connected to the driver element, which pulls or pushes the driver element, thereby stretching the blood vessel. One variation of this embodiment is illustrated in FIG. 12, which shows device 200 having driver element 210 attached to wire 250, which is enclosed in wire sheath 252. The wire 250 passes through an appropriately sized aperture in the resting member 212. Such a wire could, for example, be a made of super elastic material such as alloys of nickel and titanium. The wire can be driven by a piezo-actuator or other linear motor, by a hydraulic cylinder or actuator powered by an implanted pump or by transcutaneous injection of a fluid, by winding the wire on a rotating reel or attached to a lead screw configured to produce linear motion where either is powered by electric or hydraulic rotary actuators, or by other suitable means for pushing/pulling a wire described above or known to those skilled in the art.

Figure 13:
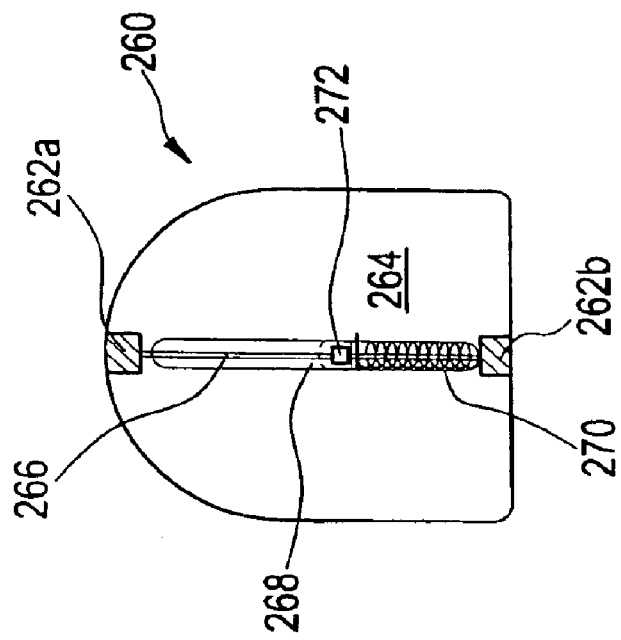
FIG. 13 is a rear view of one embodiment of a stretching device comprising a moveable driver element and fixed posts, wherein the driver element movement is guided and driven by a guide rod and a spring, respectively.

Another means for moving the driven element is illustrated in FIG. 13, which shows a base plate 260 from a side distal the blood vessel and driver elements (not shown). Support members 262a and 262b protrude from surface 264 and support both ends of guide rod 266 secured therebetween. The guide rod 266 is located parallel to and slightly spaced apart from the surface 264. The base plate includes linear slot 268, which extends through the base plate and approximately between the support members 262a and 262b. The centerline of the slot 268 and guide rod 266 if shown in FIG. 13 would be identical. Spring 270 is fitted over the guide rod 266 and can be expanded or contracted along its length to move a driver element 272 slidably connected to the guide rod 266.

Figure 14:
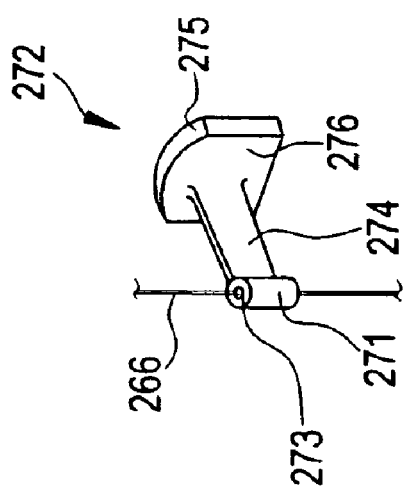
FIG. 14 is a perspective view of a preferred embodiment of a driver element suitable for use with a guide rod.

FIG. 14 illustrates one embodiment of driver element 272, wherein guide rod 266 slidingly engages the driver element through aperture 273 in distal portion 271 of the driver element. Flange 274 of the driver element 272 would mate with the slot in the baseplate so that the spring can move the driver element as needed. The lateral surface 275 of proximal portion 276 of the driver element would engage the blood vessel being stretched. It will be appreciated that assembly of the driver element, spring, guide rod, and the base plate can be facilitated by enlargement of the slot at one of its ends to permit the passage of part of the driver element.

Figure 15:
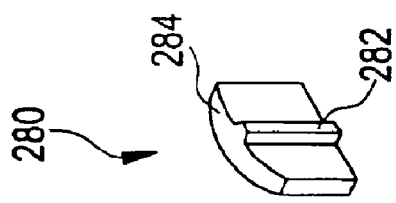
FIG. 15 is a perspective view of one embodiment of a driver element having a protrusion suitable for mating with a groove or slot in the body of the device and/or a cover plate.

Lateral stability for the driver element can, if needed, be provided by the use of mating slots (e.g., grooves) and protrusions in the base plate (or cover plate or both) and the driver element. For example, the base plate could be provided with one or more small thickness slots (female part), which mate with one or more small protrusions the driver element, whereby the protrusions of the driver element are in sliding engagement within the slots of the base plate. An example of such a modified driver element is illustrated in FIG. 15, which shows driver element 280. The driver element 280 includes a male protrusion 282 on one side of the element, which could mate with a corresponding slot in the cover plate of the device. The male protrusions and female slots could, of course, be reversed. The lateral surface 284 of the driver element would engage the blood vessel being stretched.

Figure 16:
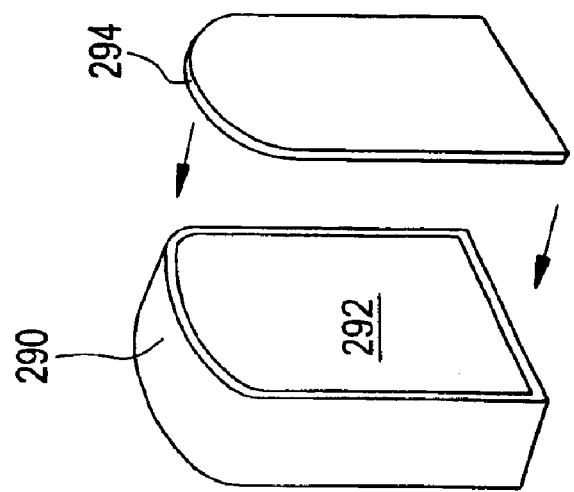
FIG. 16 is a perspective view of one embodiment of a base plate that has a recess for sealing a drive mechanism with another plate.

The spring/rod mechanism, such as shown in FIG. 13, can be covered and sealed. For example, the base plate can be modified to have a recess in which the mechanism is fit and which is enclosed with another plate. As shown in FIG. 16, a base plate 290 is made thicker and with a recess 292. The spring/rod mechanism (not shown) fits within the recess and a third plate 294 can be attached, for example, by using appropriate fasteners, adhesive bonding, ultrasonic welding, and/or other known fabrication techniques.

Figure 17A:
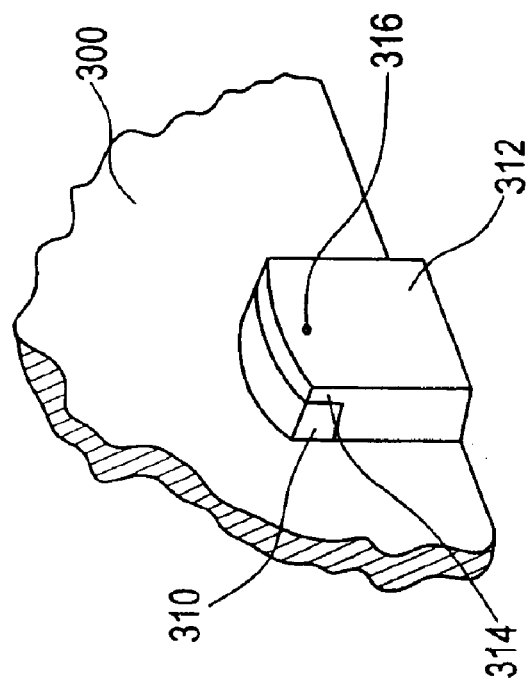
FIG. 17A is a perspective view of one embodiment of a post formed to be integral with a base plate.
Figure 17B:
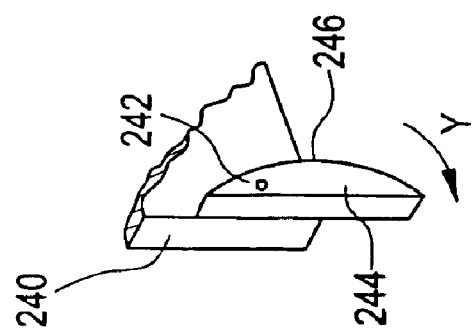
FIG. 17B is a perspective view of one embodiment of a moveable post rotatably attached to a base plate.

The radii of curvature of surfaces in contact with the blood vessel should be as large as possible so that relatively large stretching forces can be provided without collapsing the blood vessel. Examples of posts shaped for this function are illustrated in FIGS. 17A–B. FIG. 17A shows a post 234 having a curved lateral surface 236 molded into the base plate 230, wherein the post extends from a surface 232 of the base plate 230. Surface 236 could be, but is not necessarily, of constant curvature. FIG. 16B shows a similar post 244 having a curved lateral surface 246. The post 244 is rotatably attached to base plate 240 with pin 242, and is free to rotate about the axis of the pin 242 and in the plane of the base plate 240, as shown by arrow Y in FIG. 17B. In this way, the profile of the device can be changed. Specifically, rotation of the post 244 can be used to increase the profile of the device when deployed while maintaining a small profile for the device during insertion. This arrangement is useful for endoscopic deployment and provides a larger contact surface for the artery when the device is in use.

Figure 18:
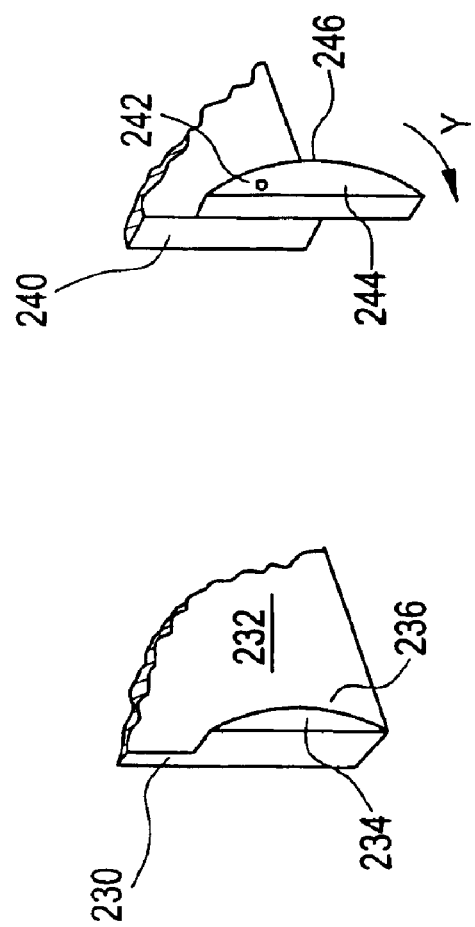
FIG. 18 is a perspective view of one embodiment of a resting member extending from a base plate, wherein the resting member includes a groove and a pin to lock the driver element in position.

FIG. 18 is useful to explain the utility of the optional cutout 205 in the cover plate 204 shown in FIG. 10. In this embodiment, the base plate 300 is designed to temporarily hold the driver element 310 in place while the device is being prepared for use. This feature is useful because the spring may be in compression and would tend to move the driver element if it were not held, complicating use of the device. The resting member 312 extends from the base plate 300 and has an L-shape as shown in FIG. 18, such that the driver element 312 can be secured between the base plate and an upper ridge 314 of the resting member 312. The thickness of the upper ridge 314 would be the same as the thickness of the cover plate 204, and the overall shape of the resting member 312 would fit flush within the cutout 205 in the cover plate 204. A pin 316 passing through an aperture in resting member 312 and into a hole in the side of the driver element 310 can serve to hold the driver element 310 in place, until it is desired to remove the pin and free the driver element to stretch a blood vessel.

In any of these embodiments utilizing a spring to supply the driving force, it will be appreciated that such a spring can be designed in a number of different ways depending on the desired force characteristic. An ordinary spring would provide constant stretch. A spring having a nonlinear or a constant force-deformation response could also be used. Yet another alternative is a spring fabricated of shape memory materials so that its stiffness or shape can be changed as stretching progresses or periodically. Such a spring could act in series or parallel with another spring designed as described above. Shape memory materials can change their shape in response to changes in their temperature. Nickel-titanium alloys, which exhibit super-elastic and shape-memory effects, are particularly suitable. Shape memory nickel-titanium alloys and certain polymeric materials can be fabricated to change shape from straight to curved as the material changes temperature. Examples of shape memory polymers are described, for example, in PCT WO 99/42528 and U.S. Pat. No. 6,160,084, which are incorporated herein.

This effect can be used to provide dynamic loading of the blood vessel by using heating means to heat the spring to change its temperature and thus its shape and/or stiffness. For example, the heating could be resistive heating of the spring by electric current (e.g., from a battery or capacitor). Periodic application of electric current can provide the dynamic loading as described above. An example of a dynamic load produced in this way is the application of short-term, large stretching forces produced whenever the shape memory material reaches its transition temperature. The forces would decrease when the current is removed and the wire cools returning the spring to its rest shape. The combination of shape change and shape recovery produces the desired dynamic, periodic load. Other means of heating the wire, such as electromagnetic fields through the skin, are also envisioned. Control of the current application can be accomplished using devices and methods described herein or known to those skilled in the art.

Yet another way of controlling the movement of the driver element is to provide a motor driven cam on which a spring-driven driver element can ride. Such an arrangement is familiar to those skilled in the art of mechanical system design.

Foldable Design

These devices are very similar in structure and function as the non-fold versions described above, except that these devices advantageously can "fold" to yield a smaller, narrower cross-sectional profile to facilitate minimally invasive in vivo insertion, preferably using standard, off-the-shelf endoscopic hardware. These embodiments also make possible devices having a wide range of aspect (length/width) ratios. This characteristic is important because it affects how much (i.e., the length) a blood vessel can be grown, as well as the size of the forces that can be applied to the blood vessel during the stretching process.

Figure 19:
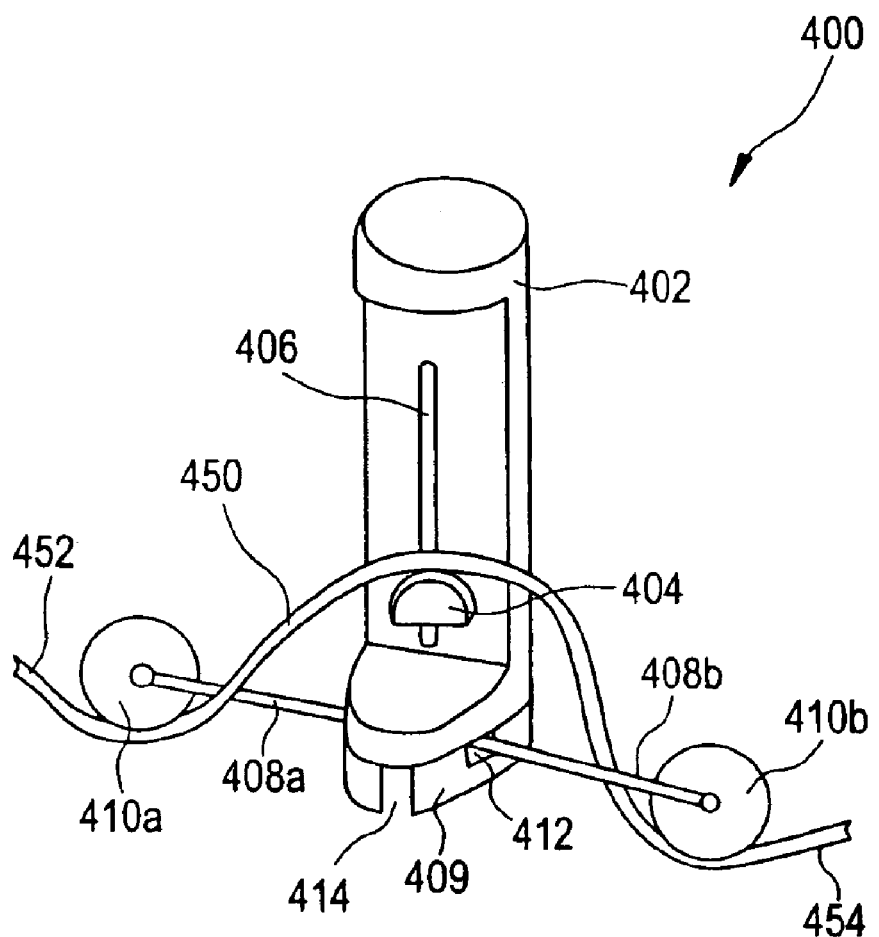
FIG. 19 is a perspective view of one preferred embodiment of a stretching device comprising a moveable driver element with a pair of moveable arms and posts in the deployed position.

One preferred embodiment of such a device is illustrated in FIG. 19. FIG. 19 shows device 400 in its deployed configuration with a blood vessel 450. The device 400 includes a cylindrically shaped body 402, which preferably houses the electromechanical or other means of moving the driver element 404 along slot 406. The mechanism for moving the driver element 404 can include any of the various means for producing the requisite linear motion that are described herein or known to those skilled in the art of mechanical design. It can be seen that as the driver element 404 moves up, the blood vessel 450 is stretched transverse to its length. The distal end 452 and proximal end 454 of the blood vessel 450 are tethered by the tissue naturally surrounding blood vessel 450, but may be further anchored using sutures or other means of fixation, as appropriate, at the distal and proximal ends. Device 400 further includes arms 408*a* and 408*b*, which extend from and are hinged at the lower end portion 409 of the body 402. Wheels 410*a* and 410*b* (which function like the posts in the non-fold design) are rotatably attached to the ends of arms 408*a* and 408*b*, respectively, distal the body 402.

FIGS. 20A–B show the device in its "folded" configuration, i.e., before deployment, in a side view (FIG. 20A) and in a front view (FIG. 20B). As can be seen, the arms 408*a/b* and wheels 410*a/b* fold down so as to reduce the cross-sectional profile of device 400 so that it can be more readily inserted through a standard endoscopic trochar. Once inserted, the arms 408*a/b* and wheels 410*a/b* can be deployed as shown in FIG. 19.

A wide variety of mechanisms to effect the folding and deployment can be devised by those skilled in the art of mechanical design. FIGS. 19 and 20 can be used to describe one such scheme. In this scheme, the lower end portion 409 of the body 402 is made so that it has two "locked" configurations. One is shown in FIGS. 20A and 20B and the other, representing a ninety degree axial rotation of the lower end portion 409, is shown in FIG. 19. When in either of these two "locked" configurations, the lower end portion 409 resists rotation about the longitudinal axis of the body 402. Such resistance can be provided, for example, by a protrusion from the lower end portion into mating intrusions into the cylindrical body of the device. The lower end portion 409 also is designed so that it can move in the axial direction, away from the body 402, as shown by arrow K. This can be achieved by a central round shaft in the body 402 of the device 400 and a mating central hole in the lower end portion 409, wherein the lower end portion 409 is spring loaded in the axial direction so that any axial movement in direction of arrow K tends to be recovered as the lower end portion 409 tries, under spring load, to return the spring towards equilibrium by moving in direction shown by arrow L. When in either one of the two locked configurations, the lower end portion 409 is prevented from rotating about the axis of the device by the protrusion and mating intrusions previously described. Such protrusion and intrusions would be of a length and depth, respectively, that when the lower end portion 409 is moved axially, it could, if moved sufficiently, be freed of its axial rotational lock. When so freed, the lower end portion 409 can be freely rotated about the axis of the body 402. Upon rotation to either the configuration shown in FIG. 19 or FIG. 20A or FIG. 20B, the lower end portion 409 can again be rotationally locked. This occurs when the spring induced axial motion (in the direction of arrow L) results in the interlocking of the aligned protrusion with one of the other of the intrusions.

The lower end portion 409 includes upper slots 412 and lower slots 414.

There are two slots here, but the device could also be designed with one continuous slot, or with more than two slots, if desired. After insertion of device 400 into a donor patient, the arms 408a/b (with wheels 410a/b) are free to move about their hinged connection to lower end portion 409, in the direction of the curved arrows M shown in FIG. 20A, toward and into their deployed position shown in FIG. 19. This causes the arms 408a/b to move into slots 414. Once the arms 408a/b are horizontal (i.e., perpendicular to the axis of the body 402), the lower end portion 409 can be moved axially, unlocked, rotated ninety degrees, and released and re-locked as described above. In so doing, slots 412 will lock the arms 408a/b in place, as shown in FIG. 19. Once the arms 408a/b are locked, the device 400 is ready for blood vessel loading and stretching.

The device 400 preferably includes suitable top and bottom plates (not shown in FIG. 19) that isolate, as much as possible, the device from the surrounding tissue and body fluids and minimize the mechanical influences of external forces that might tend to move the device. FIG. 21 illustrates one embodiment of a bottom plate 420. The plate can sutured or otherwise held in place by various means of attachment. FIG. 21 shows the plate 420 with sutures 422. The plate 420 further includes snaps 424 for attaching the plate 420 to the back of the body of a device, such as that of FIG. 19. Other attachment means, such as tapped holes, threaded protrusions, or other fasteners can be used to connect the bottom plate (and the top plate) to the body of the device.

When implanting the device, a tool, such as tool 430 in FIG. 21, can be used to stretch a blood vessel 450 over wheels 410 in the direction of arrow N, thereby properly seating the blood vessel 450 in the device. (Note that only the wheels of the device are shown in FIG. 21.) The device then can be secured to the bottom plate. Once the bottom plate and device are in place, a suitable top plate can be installed so that the device is, to the extent possible, isolated from its surroundings.

Other Features of Either Design

The methods and devices described herein optionally can include growth factors or other growth stimulating agents (e.g., hormones) to further enhance blood vessel growth. For example, such growth stimulating agents can be delivered to the blood vessel by impregnating the materials forming the device or by providing a suitable coating or reservoirs in the device that can contain and controllably release such agents during the extension process. Examples of such growth factors include vascular endothelial growth factor (VEGF), endothelial cell growth factor (ECGF), basic fibroblast growth factor (bFGF), and platelet derived growth factor (PDGF). Biocompatible polymeric materials for controlled release that are known in the art for drug delivery (see e.g., U.S. Pat. No. 5,879,713 to Roth et al.) can be adapted for use with the devices described herein. The devices and methods also can be used in combination with external electric, magnetic, or electromagnetic fields applied as a growth stimulus (see e.g., U.S. Pat. No. 4,846,181 to Miller).

The devices also can optionally include appropriate drugs (e.g., therapeutic or prophylactic agents) impregnated into or coated to structural components, for example to minimize infections, inflammatory reactions, scar tissue formation, adhesion formation, and/or other adverse tissue reactions. For example, where tissue growth is to be avoided, certain antifibrotic agents may be present, such as 5-fluourouracil or mitomycin. The device may be more generally provided with coatings that are antibiotic or anti-inflammatory.

The devices also can be enclosed in a suitable sheath to limit adhesion formation and/or infiltration by body fluids while implanted in vivo, or be impregnated or coated with materials selected to reduce adhesion formation as known in the art. Examples of such coating materials include, but are not limited to, parylene, polytetrafluoroethylene (e.g., TEFLON™) and chromium (e.g., ME-92™, Armoloy Corp.), which can be used to coat a variety of other metal and polymer substrates.

The devices and methods of use thereof described herein are further described by the following non-limiting examples.

EXAMPLE 1

In Vivo Vessel Stretching to Stimulate Cell Division

Leung et al., *Science* 191:475–77 (1976) showed that cyclic stretching stimulates synthesis of matrix components in arterial smooth muscle cells in-vitro. Subsequent studies in arterial tissue have been limited to the effects stretching on cells attached to a membrane in cell culture (see, for example, Birukov, et al., *Molecular & Cellular Biochem.* 144:131–39 (1995); Costa, et al., *FASEB J.* 5:A1609–7191 (1991)) or in a vascular graft construct (Kanda, et al., *Cell Transplantation* 4(6):587–95 (1995)). No known studies, however, have analyzed the effect of stretch on cells in intact vessel walls. Therefore, a study was made of porcine carotid arteries in an organ culture system developed by Conklin (Conklin, B. *Viability of Porcine Common Carotid Arteries in a Novel Organ Culture System* MS Thesis, Georgia Institute of Technology, 1997), in order to determine the effect of axial stretching on smooth muscle cell division in an intact vessel. See also Han, H. C., Vito, R. P., Michael, K., Ku, D. N., "Axial Stretch Increases Cell Proliferation in Arteries in Organ Culture," *Advances in Bioengineering. ASME, BED* 48:63–64 (2000).

Left and right external carotid arteries were obtained at slaughter, one for testing and the other serving as a control. Both vessels were immersed in cell culture media containing DMEM (Sigma D 1152), sodium bicarbonate (3.7 g/L, Sigma), L-glutamine (2 mM, Sigma), antibiotic-antimycotic solution (10 ml/L, Gibco), and calf serum (CS 10%, Integren). The vessels were perfused with the same media with the addition of Dextran (5% by weight, MW 282,000 Sigma). The test and control specimen both were maintained at body temperature and subjected to pulsatile flow in the physiological range. The control specimen was restored to and maintained at the in-vivo length, which corresponds to a stretch ratio of 1.5, for the duration of the experiment. The test specimen was stretched an additional 30% to a stretch ratio of 1.8 over the first two and one-half days of the five day experiment.

Bromodeoxyuridine ("BRDU") staining was used to compare the number of cells that were dividing in the test and control specimens. On the fifth day, the specimens were pressure-fixed with formalin and histologic slides prepared for cell counting using light microscopy. The BRDU was added on day four and the test specimen showed that 6.8+/−2.8% of the cells were dividing, while only 3.08+/−2.9% of the cells were dividing in the control specimen. The results clearly suggest that axial stretching can be used to enhance cell division in blood vessels, and should therefore be useful in the growing vessel segments for use in creating blood vessel grafts.

Modifications and variations of the present invention will be obvious to those of skill in the art from the foregoing detailed description. Such modifications and variations are intended to come within the scope of the following claims.

We claim:

1. A device for distending and growing a blood vessel of a human or animal comprising:
   a stretching mechanism attachable directly to a blood vessel at at least two attachment positions thereon; and
   means for operating the stretching mechanism to cause the blood vessel portion between said at least two attachment positions to be stretched axially,
   wherein the device is effective to grow the blood vessel tissue.

2. The device of claim 1, wherein said at least two attachment positions are in a fixed position relative to one another.

3. The device of claim 1, wherein the operating means can displace said at least two attachment positions away from each other over a period of time.

4. The device of claim 3, wherein the stretching mechanism comprises a pair of opposed straps that can be removably secured at said two attachment positions.

5. The device of claim 4, wherein the stretching mechanism further comprises a pair of push/pull rods each connected to the opposed straps.

6. The device of claim 1, wherein the stretching mechanism can stretch the vessel portion rectilinearly, curvilinearly, or in a combination thereof.

7. The device of claim 1, wherein the stretching mechanism can stretch the vessel portion curvilinearly.

8. The device of claim 1, further comprising a controller for controlling the operating means.

9. The device of claim 1, wherein the means for operating the stretching mechanism comprises a prime mover that is electronically or hydraulically driven.

10. The device of claim 1, wherein the stretching mechanism comprises an inflation or expansion means disposed between said at least two attachment positions.

11. The device of claim 10, wherein the inflation means comprises a balloon.

12. The device of claim 10, further comprising a rigid surface having (i) two opposing flexible ends for removably securing to said at least two attachment positions, and (ii) a pair of plates projecting from the rigid surface, wherein the plates are substantially parallel to each other between the flexible ends and the inflation or expansion means is disposed between the plates.

13. The device of claim 1, wherein the stretching mechanism comprises a curved or angled surface having two opposing flexible ends that can be removably secured at said two attachment positions, wherein the flexible ends can be drawn towards one another to effect said stretching.

14. The device of claim 1, wherein all or a portion of the device is radioopaque.

15. A method for distending and growing a blood vessel of a human or animal comprising:
   attaching a stretching mechanism to a blood vessel at at least two attachment positions thereon; and
   operating the stretching mechanism over a period of time to cause the blood vessel portion between said at least two attachment positions to be stretched axially and to grow.

16. The method of claim 15, wherein the stretching occurs in vivo.

17. The method of claim 15, wherein the blood vessel is excised from the human or animal before attachment of the stretching mechanism.

18. The method of claim 15, wherein said at least two attachment positions are displaced away from each other over a period of time.

19. The method of claim 15, wherein said at least two attachment positions remain in a fixed position relative to one another during said operating of the stretching mechanism.

20. The method of claim 15, wherein the stretching mechanism is operated intermittently.

21. The method of claim 15, wherein the stretching mechanism is operated continuously.

22. The method of claim 15, wherein the stretching mechanism is operated cyclically.

23. A method of forming an autologous vascular tissue graft for a human or animal in need thereof, comprising:
   (a) distending a donor blood vessel by use of a method which comprises
      (i) attaching a stretching mechanism directly to the donor vessel at at least two attachment positions thereon, and
      (ii) operating the stretching mechanism gradually or repeatedly over a period of time sufficient to axially stretch the donor vessel between said at least two attachment positions to a desired length;
   (b) excising a stretched portion of the donor vessel; and
   (c) suturing the ends of the donor vessel to repair the donor vessel.

24. The method of claim 23, wherein the device or a portion thereof is radioopaque, further comprising taking an x-ray of said radioopaque device or portion thereof to determine the extent of stretching.

25. The method of claim 20, wherein the stretching mechanism further comprises a microprocessor, the method further comprising programming the microprocessor to control the stretching.

26. A method of forming an autologous vascular tissue graft for a human or animal in need thereof, comprising:
 (a) excising a donor vessel portion of a blood vessel from the human or animal; and
 (b) distending the donor vessel portion by use of a method which comprises
  (i) attaching a stretching mechanism directly to the donor vessel portion at at least two attachment positions thereon, and
  (ii) operating the stretching mechanism gradually or repeatedly over a period of time sufficient to axially stretch the donor vessel portion between said at least two attachment positions and to grow the donor vessel to a desired length.

27. The method of claim 26, wherein the stretching is performed with the donor vessel portion in a medium for cell growth.

28. The method of claim 15, wherein the stretched and grown blood vessel has a length greater than 30% of the blood vessel.

29. The method of claim 26, wherein the stretched and grown donor vessel has a length greater than 30% of the donor vessel portion during excision.

30. An implantable medical device for growing a segment of a blood vessel of a human or animal for subsequent use as a donor blood vessel comprising:
 a stretching mechanism attachable directly to a blood vessel at at least two attachment positions thereon; and
 means for operating the stretching mechanism to cause the blood vessel portion between said at least two attachment positions to be stretched axially to induce growth of the blood vessel tissue in vivo.

* * * * *